(12) United States Patent
Kropf et al.

(10) Patent No.: US 8,157,870 B2
(45) Date of Patent: Apr. 17, 2012

(54) PROSTHESIS FOR REPLACING THE SURFACE IN THE AREA OF THE BALL OF BALL-AND-SOCKET JOINTS

(75) Inventors: Philipp Kropf, Cham (CH); Ralph Hertel, Muri (CH)

(73) Assignee: Synthes USA, LLC, West Chester, PA (US)

( * ) Notice: Subject to any disclaimer, the term of this patent is extended or adjusted under 35 U.S.C. 154(b) by 1033 days.

(21) Appl. No.: 10/597,847

(22) PCT Filed: Feb. 21, 2005

(86) PCT No.: PCT/CH2005/000099
§ 371 (c)(1),
(2), (4) Date: Aug. 9, 2006

(87) PCT Pub. No.: WO2005/079709
PCT Pub. Date: Sep. 1, 2005

(65) Prior Publication Data
US 2007/0162149 A1    Jul. 12, 2007

(30) Foreign Application Priority Data
Feb. 20, 2004 (EP) .................................. 04003943

(51) Int. Cl.
*A61F 2/36* (2006.01)
(52) U.S. Cl. ................................................. 623/23.12
(58) Field of Classification Search .... 623/19.11–19.13, 623/14.12, 23.42, 23.43, 23.11, 23.12, 23.4, 623/22.4, 22.42
See application file for complete search history.

(56) References Cited

U.S. PATENT DOCUMENTS

| | | | |
|---|---|---|---|
| 4,328,593 A | 5/1982 | Straumann et al. | |
| 4,332,036 A * | 6/1982 | Sutter et al. | 623/23.42 |
| 5,549,704 A | 8/1996 | Sutter | |
| 6,048,365 A | 4/2000 | Burrows et al. | |
| 2003/0163202 A1 * | 8/2003 | Lakin | 623/22.15 |

FOREIGN PATENT DOCUMENTS

| | | |
|---|---|---|
| DE | 2751535 | 5/1979 |
| FR | 2578739 | 9/1986 |
| FR | 2737970 | 2/1997 |

OTHER PUBLICATIONS

International Search Report for International Application No. PCT/CH2005/000099, dated May 19, 2005.

* cited by examiner

*Primary Examiner* — Thomas J Sweet
*Assistant Examiner* — Megan Wolf
(74) *Attorney, Agent, or Firm* — Fay Kaplun & Marcin, LLP

(57) ABSTRACT

A prosthesis for replacing a surface in an area of a ball of a ball-and-socket joint includes a spherical shell section having an outer surface that is configured to lie in an articular fossa and is for attachment to a surface. The shell section having a cavity for receiving a bone end. The prosthesis also includes a crown that partitions the cavity of the shell section into a first cavity and a second cavity, wherein a shape of the shell section is at least a section of a hemisphere and a free edge of the crown lies in the same plane as a free edge of the shell section.

20 Claims, 4 Drawing Sheets

PROSTHESIS FOR REPLACING THE SURFACE IN THE AREA OF THE BALL OF BALL-AND-SOCKET JOINTS

REFERENCE TO RELATED APPLICATIONS

This is a U.S. National Phase application under 35 U.S.C. §371 of International Patent Application No. PCT/CH2005/000099, filed Feb. 21, 2005, and claims priority of the European Patent Application no. 04 003 943.0, which was submitted on Feb. 20, 2004 and to whose entire disclosure reference is herewith made.

TECHNICAL FIELD

The invention relates to a prosthesis for replacing the surface in the area of a ball of ball-and-socket joints, a procedure for implantation of such a prosthesis and furthermore a material set for manufacture of a particular embodiment of such a prosthesis as well as a set of prostheses of various sizes.

BACKGROUND

Prostheses of this type are used with ball-and-socket joints, particularly with shoulder and hip joints. Fundamentally there are with prostheses for ball-and-socket joints two different solution versions.

In a first version, the ball is entirely or at least half detached and replaced by a prosthesis, with this having a shaft that is inserted into the remaining bone or its medullary space. Such shaft prostheses are especially suited for older persons and/or in a case of bone fractures, for example femoral neck fractures.

With a second version, merely the surface of the bone or cartilage is at least partially replaced. One speaks in this case of "surface replacement prostheses," "resurfacing prostheses," or also "cap prostheses." Such prostheses are for example offered under the trade names "Durom" and "Copeland." These prosthesis types have the advantage that their implantation is minimally invasive. The duration of operation is shorter. For a replacement of the prosthesis, there are more possibilities. In particular a reverse operation is offered, in which the prosthesis is replaced by a shaft prosthesis, as it is described above.

One problem with surface replacement prostheses however consists in that their attachment mostly is harder than in prostheses with a shaft. There are various approaches to implement the attachment.

Thus there are surface replacement prostheses which consist only of a cap, but for this in essence they surround the entire joint ball. According to appearances this at least leads to a better distribution of forces, however more bone material must be removed and the stability to tensile forces is imperfect under certain circumstances.

Additionally there are surface prostheses that have a handle, whereby its length corresponds roughly to the ball diameter. Thereby the forces are distributed to additional contact surfaces and the prosthesis is better centered on the joint ball. However the solution is imperfect, among other things because the handle is subject to lever forces and thus under certain circumstances can lead to a loosening of the prosthesis.

In some cases also with the known prosthesis the problem is posed that the bone necrotizes in the area of the joint head, and thus particularly at the contact surfaces with the prosthesis, U.S. Pat. No. 4,328,593 shows a surface prosthesis with a cap that is larger than a hemisphere and has a cylindrical, hollow handle that projects far over the lower edge of the cap. U.S. Pat. No. 5,549,704 shows a surface prosthesis similar to the named US document. FR-A-2 578 739 shows a surface prosthesis in which a part of the cap is smaller than a hemisphere and a flap part projects over the cap. For attachment a threaded bolt is provided into which a peg of the cap engages. FR-A-2 737 970 shows a surface prosthesis with a cap that is smaller or larger than a hemisphere and which has a central handle.

SUMMARY

Therefore the task is set of preparing a prosthesis of the type named initially, which at least partially avoids the disadvantages named above.

This problem is solved with a prosthesis for replacing a surface in an area of a ball of a ball-and-socket joint. The prosthesis includes a spherical shell section having an outer surface that is configured to lie in an articular fossa and is for attachment to a surface. The shell section having a cavity for receiving a bone end. The prosthesis also includes a crown that partitions the cavity of the shell section into a first cavity and a second cavity, wherein a shape of the shell section is at least a section of a hemisphere and a free edge of the crown lies in the same plane as a free edge of the shell section.

A prosthesis of this kind has the advantage that its attachment is stable and due to the large adjoining surface, the forces acting between bone and prosthesis are well distributed. Additionally, with proper placement and dimensioning, the crown engages directly into the load-bearing and intact structures of the bone, whereby a good long-term stability is achieved. The implantation of the prosthesis is slightly invasive. The spherical shell section with a height h is smaller or at most equal to the radius of the ball, and thus smaller or at most equal to a hemispherical ball shell. Preferably the height h is between 70-85% of the ball radius. This suffices to cover the cartilage covered articulation surface. A ball that is closed can no longer be treated starting at the tapering location. The crown is in essence equal to the ball section or terminates in its diameter plane and is even shorter if necessary. This suffices for the anchoring in bone. In a repeat procedure as a revision, with a saw, sawing can be done flush on the visible ball section. This means that during sawing the section direction is visible and difficult section or tearing out of a long crown is not necessary.

By having the ball section be smaller than or equal to the ball radius, the crown can largely be outwardly positioned. Thus the crown surface is maximized and the (loaded) contact surface to bone is increased and thus the stability is enhanced.

Preferably the crown grows proportionally to the implant (proportionality, i.e., the bigger the ball diameter, the larger the crown). This corresponds to anatomy and effects an especially good stability of attachment of the prosthesis.

With the invention-specific prosthesis, only small amounts of bone material need be removed and thus much bone is retained. The operation duration is relatively short.

Preferably the crown wall is not equally thick overall, rather it runs conically and increases in the direction of the attachment point. Thereby during insertion, a certain, controlled pressure is built up, which improves the stability. Further, preferably one to three sides of the crown are parallel, 1-3 sides conical. Depending on the arrangement the pressure is applied in controlled fashion in one or more directions. In another preferred embodiment, the inner sides of the crown are parallel and the outer sides run conically. Thereby the pressure that arises during insertion, is built up toward the exterior, in the direction of the inner side of the ball section. The bone section is wedged between the crown and inner side of the ball section. Further, it is preferred to provide the crown with holes. Thus can the blood-infused bone in the interior of the crown "survive." Only an annular segment of bone is removed, which is replaced by the crown with holes. Through the holes in the ring the bone segments can again grow into each other. Preferably there follows after the cylindrical piece a conical piece with circumferential small holes (no threadings), which offer stability against tearing out. They act like barbs.

The advantages named also are gleaned from the subjects of the further independent claims.

BRIEF DESCRIPTION OF DRAWINGS

Further advantages and preferred embodiment examples are gleaned from the dependent claims as well as the description now following aided by the figures. Shown are:

DETAILED DESCRIPTION OF PREFERRED EMBODIMENTS

Figure 1:
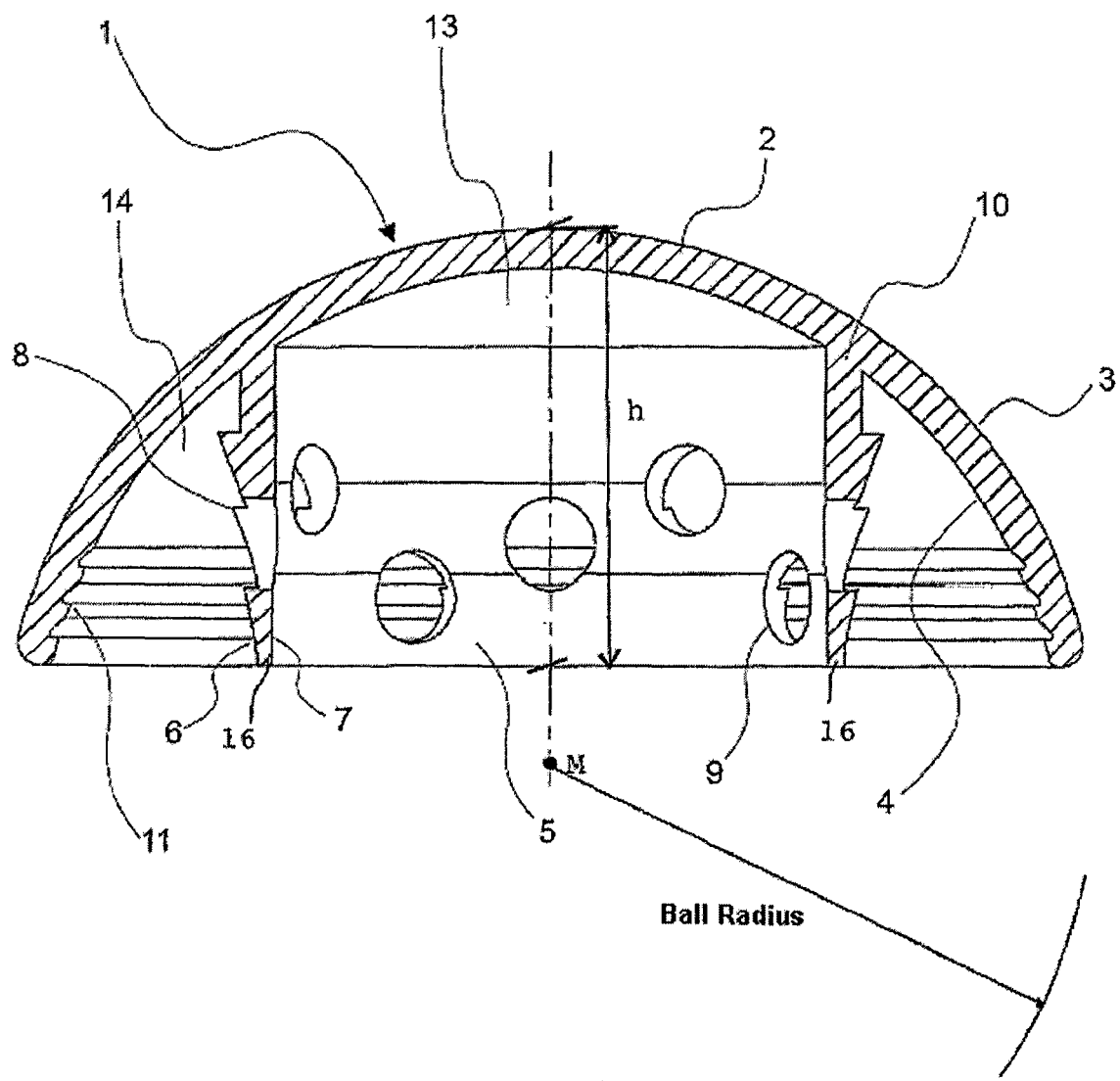
FIG. 1 a cross-section of a prosthesis according to one embodiment the present invention.
Figure 2:
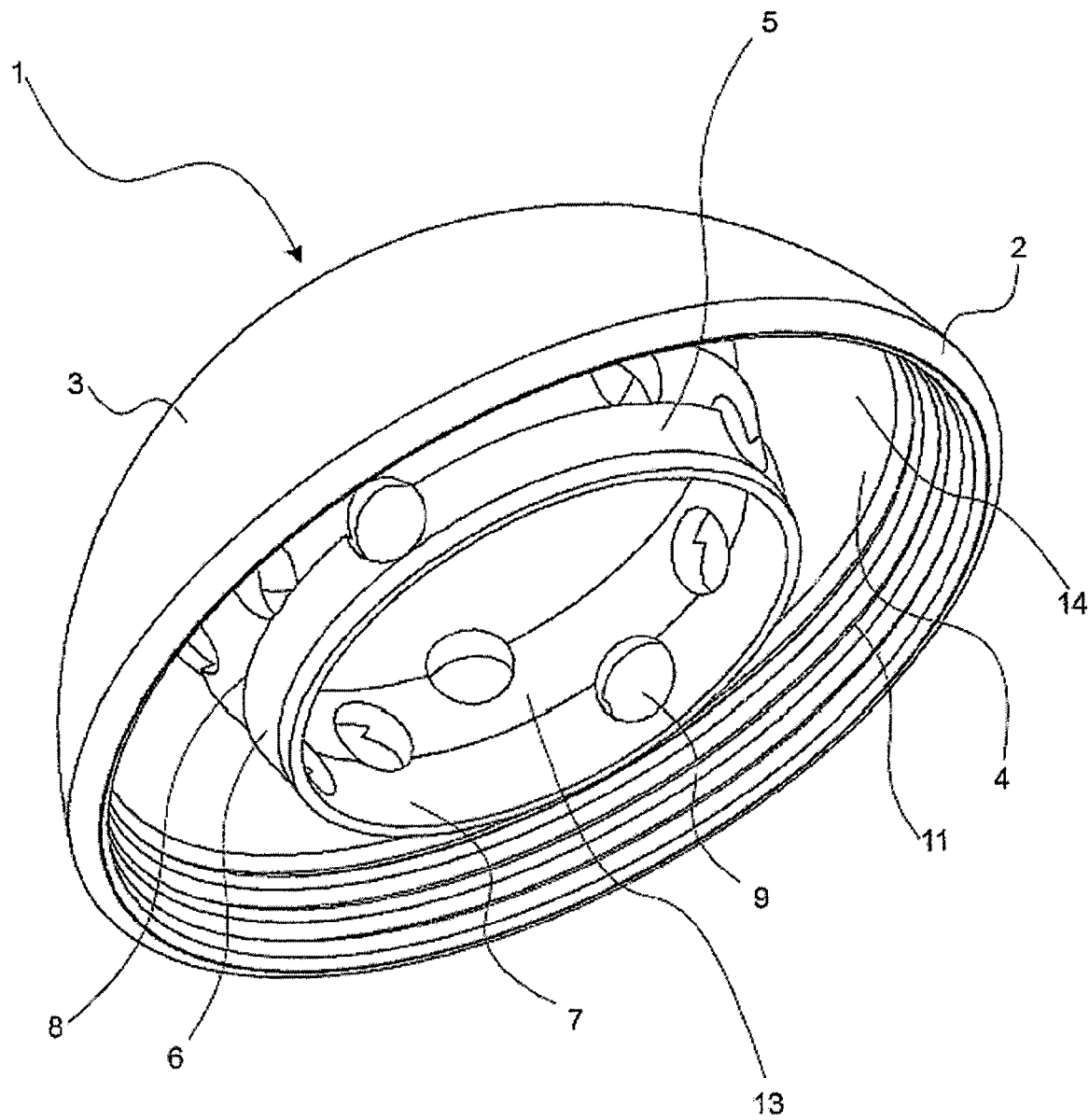
FIG. 2 a perspective view of the prosthesis of FIG. 1.

FIG. 1 shows a cross-section through a preferred embodiment of the invention-specific prosthesis. FIG. 2 shows a perspective view of that same prosthesis. The prosthesis serves for partial replacement of the surface of a ball of a ball-and-socket joint, as for example the femoral head. The prosthesis 1 consists in essence of a spherical shell section or spherical shell portion 2 and a crown 5 placed therein.

The spherical shell section 2 has the form of a hemisphere or preferably the form of a section of a hemisphere. This has the advantage that during implantation only a partial resection of the joint ball surface must be undertaken. The spherical shell section 2 is thus preferably somewhat smaller than a hemisphere, i.e. it preferably extends at an angle of 145 to 180 degrees. The spherical shell section 2 can also be designated as a "cap" or, if it, as in the shown embodiment, is in essence hemisphere-shaped, as a "hemisphere." Especially preferred is a cap, thus a spherical shell segment, that is smaller than a hemisphere and especially has a height h of only 65%-90% and especially 70%-85% and especially about 80% of the ball radius, corresponding to an angle from the midpoint M outward of about 117 to 162 degrees respectively, 126 to 153 degrees respectively, about 144 degrees respectively, if a hemisphere is 180°. In FIG. 1 the height h of the spherical shell section is designated as well as the midpoint M of the ball.

The outer surface 3 of the spherical shell section 2 is configured to lie in an articular fossa. The outer surface 3 is particularly smooth, so that it can move well in the articular fossa. Likewise the articular fossa can be a prosthesis. On the inner surface 4 a fluting 11 is provided, which is formed by the annular groove running through in the area of the edge. An embodiment of the spherical shell segment 2 with a relief of that kind or of another nature leads to better holding of the prosthesis.

The crown 5 serves for attachment or anchoring of the prosthesis on or in the bone and/or for better distribution of support forces. Preferably it has in essence the shape of a cylindrical cover surface. Its diameter is 45 to 75 percent, particularly 55 to 65 percent, especially about 60 percent of the diameter of the spherical shell section 2. Due to this dimensioning the crown 5 engages into or on a very stable part of the bone, whereby its pipelike structure is taken into consideration. The crown 5 has an outer surface 6 and an inner surface 7. On the outer surface 6 a fluting 8 is provided in the form of annular beads passing around the crown 5. The fluting can also be provided on the inner surface 7 or on both surfaces 6, 7. An embodiment of the crown 5 with one relief of that kind or of another nature leads to better holding of the prosthesis. On its free end the crown preferably has a short cylindrical section 16 (insertion), that facilitates insertion of the implant into the annular groove in the bone. The crown 5 is placed at least partially in the spherical shell section 2. Due to the crown 5, the open cavity formed by the spherical shell section 2 to admit a bone end is subdivided in essence into an interior, first cavity 13 and an exterior, annular second cavity 14 that is situated around it. The expression "in essence" in this connection is to indicate that the crown 5, as explained more in detail further below, may have recesses which connect the two cavities 13 and 14. The cavities 13, 14 serve to admit the bone end and therefore are open on the side facing the bone. The opening of the first cavity 13 is circular-surface-shaped, that of the second cavity 14 is annular. In the case of an implanted prosthesis the bone projects into these cavities 13, 14. Particularly after an intergrowth phase, the cavities in essence are filled entirely with bone or with tissue similar to bone. In the crown 5, preferably about five to ten recesses 9, particularly in essence round holes, are provided. Through these, the bone situated in the two cavities 13, 14 can grow and come together. This makes possible a better blood infusion of the bone and leads to a better holding of prosthesis 1, especially also with tensile forces. The recesses may also extend over the entire length of the crown, so that the crown is interrupted by gaps and/or subdivided into individual teeth. The inner surface 4 of spherical shell section 2 and the surface, i.e. the outer surface 6 and inner surface 7, of crown 5 are configured for a contact and/or a coalescence with the bone. For this the surfaces are especially rough.

Figure 4:
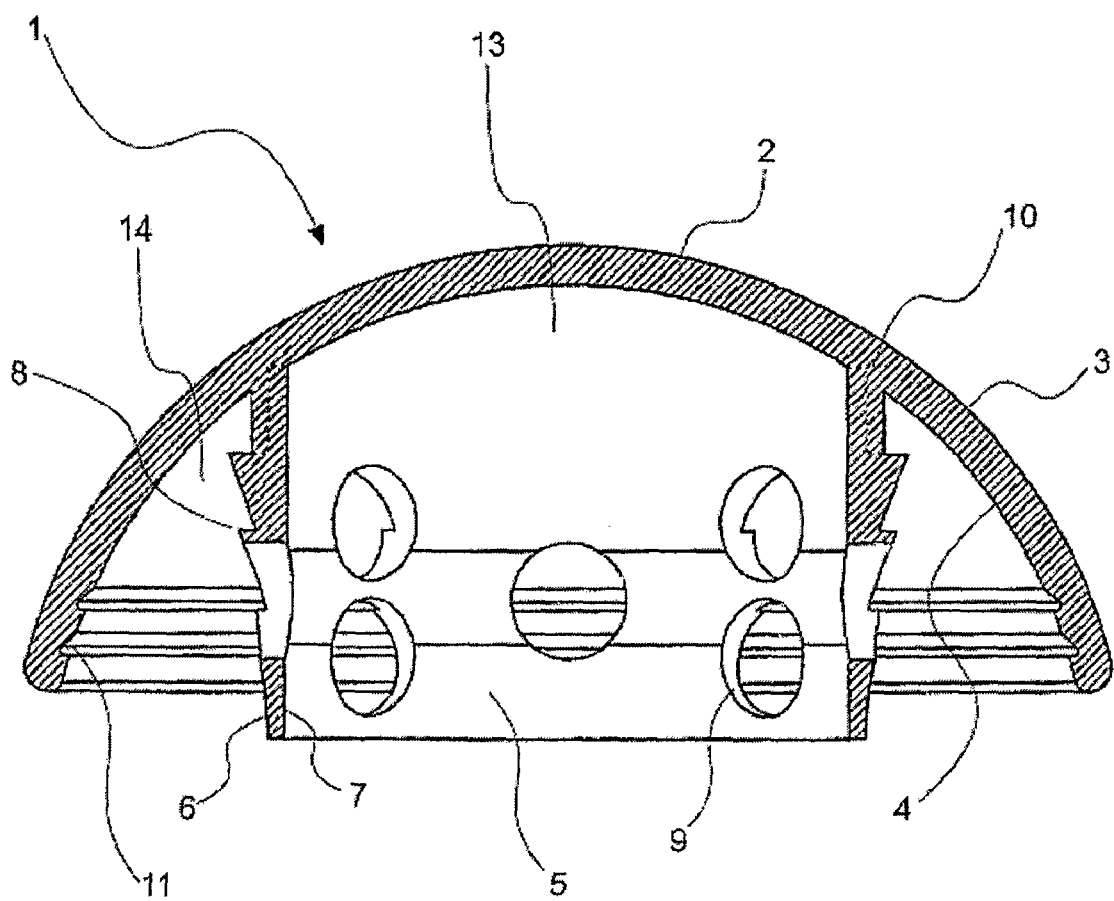
FIG. 4 is a cross-section of a prosthesis according to another embodiment of the present invention.
Figure 5:
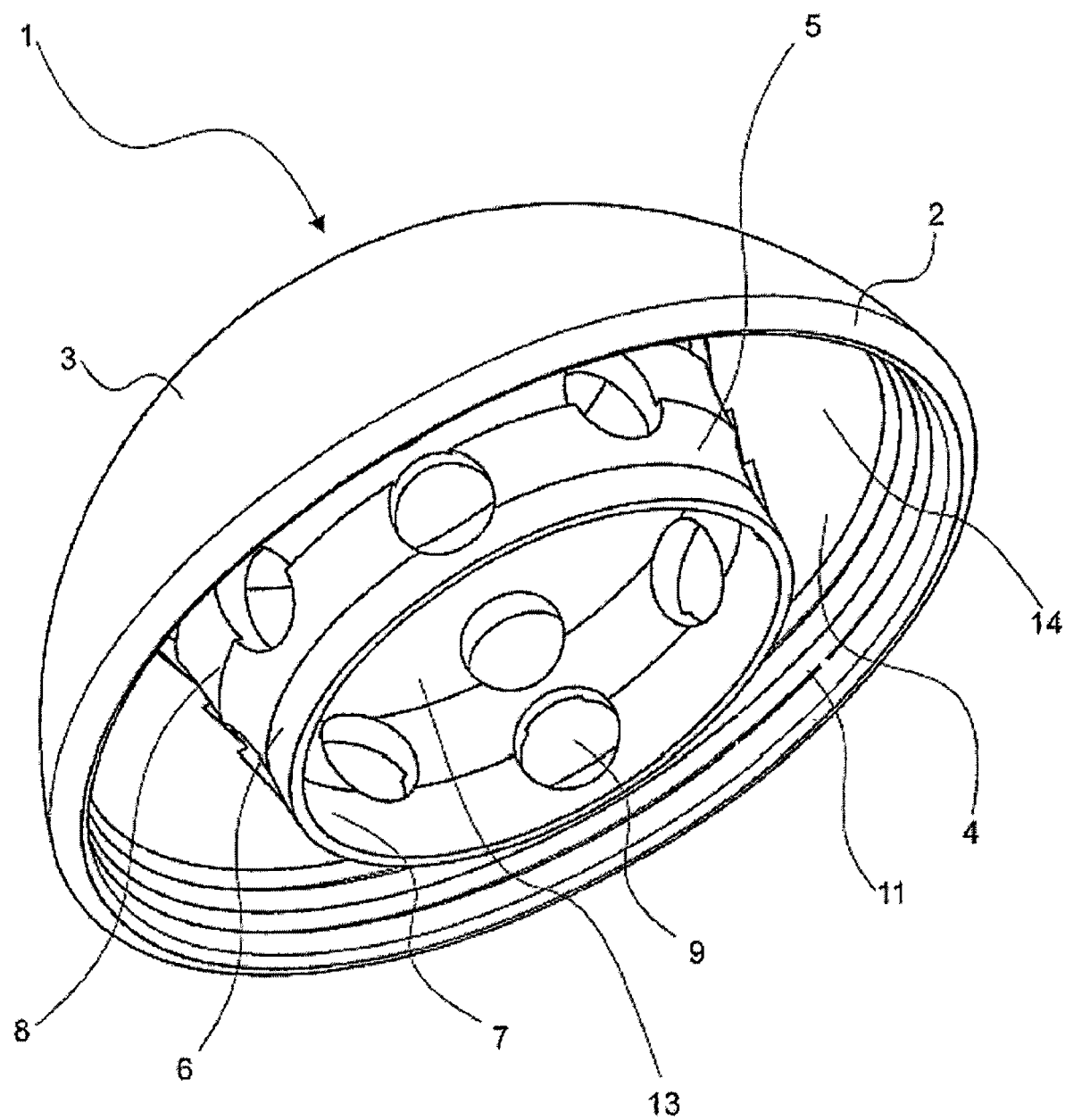
FIG. 5 shows the embodiment of FIG. 4 in a graphical representation

The crown 5 preferably is one-piece-configured together with the spherical shell section 2. Crown 5 and spherical shell 2 may however also be manufactured separately at first and then welded at a connection point 10. The crown is placed coaxial to the circular-shaped edge of spherical shell section 2, i.e. the symmetry axes of crown 5 and spherical shell section 2 lie on the same straight line. The edge of crown 5 preferably runs in essence in the same plane as the edge of spherical shell section 2 (FIGS. 1 and 2). With this embodiment the crown edge runs in the plane or projects by a small distance such as by 1 to 3 mm, above the plane in which the edge of spherical shell section 2 runs, which is depicted in FIGS. 4 and 5. Thus it is ensured that upon placement of the prosthesis, the crown 5 first contacts the prepared bones and a groove prepared for the crown 5 can be used as a directional and centering aid. The embodiment with a crown 5 that does not project significantly, thus for example only 0.2 to 5 mm or 1-3 mm, over the edge of the spherical shell section 2, has the advantage that if a replacement of the prosthesis by a shaft prosthesis is necessary, the existing prosthesis does not have to be extracted from the bone, rather can be simply sawed off together with a part of the bone. Only bone needs thereby to be sawed through. The bone-side piece of the joint ball remains in a mass sufficient for a shaft prosthesis. In a further embodiment form the crown is shorter, for example likewise 1-3 mm or 0.2 to 5 mm, than the spherical section and thus does not reach the plane of the spherical section edge.

The invention-specific prosthesis has the advantage that it logically minimizes the required bone resection. This particularly enhances the choices for possible removal operations.

In implantation of the invention-specific prosthesis, first the head of the bone is appropriately spalled and/or milled with a special tool to conform to the shape of the spherical shell section. Then an annular groove is cut into the bone, which is gauged to the dimensions of the crown. This preferably occurs with a crown miller specially provided for this. Then the prosthesis is pressed onto the bone thus prepared and/or pounded into it. No cement is required. The typical operation time can be significantly reduced in using the invention-specific prosthesis.

The invention-specific prosthesis can be generally used for ball-and-socket joints, but especially for the shoulder and the hip joint. For this the prosthesis is prepared in various sizes. The prosthesis is additionally prepared in various sizes, to enable selection of a prosthesis optimally adjusted to the anatomy or body weight of the patient.

In a further embodiment of the invention, spherical shell section and crown are produced separately, i.e., as individual parts or as a material set of individual parts. On the spherical shell section and/or on the crown, a mechanical attachment medium as for example a screw threading, a bayonet joint or a clamping device is thereby provided. By means of these the spherical shell section and crown are connected. In such an embodiment as a material set, it is possible to combine variously configured spherical shells, particularly with differing ball radii, and variously configured crowns, particularly with differing lengths and diameters, in conformity to the anatomy of the patient. Thus, particularly during the operation, can specially adapted prostheses be manufactured.

In a further embodiment of the invention, the prosthesis, instead of being beaten in or pressed on, is configured to be screwed in or screwed on. The fluting on the crown and/or the fluting on the interior surface of the spherical shell section is configured as a threading for this. Additionally, the prosthesis especially has notches and/or flattened zones as working surfaces for a turning tool.

With the embodiment shown in the figures, the crown in essence has the shape of a cylindrical cover piece. The crown, or its inner and outer surface, can however also be configured to be completely or partially conical. In a possible version, the inner surface in essence is cylindrical and the outer surface in essence conical. In a further version the inner surface in essence is conical and the outer surface in essence cylindrical. Thereby the conicity is preferred so that the wall thickness of the crown increases to the spherical shell section, for example from 1 mm at the edge up to 4 mm at the transition to the circular cylinder section. This has the advantage that upon placement of the prosthesis additional pressure is generated, which improves the holding of the prosthesis on the bone.

Further, in the embodiment shown in the figures, the crown has the ground plan of a circle. The ground plan however can be chosen to be other, for example star-shaped or in the form of an especially regular polyhedron, for example a hexagon.

Figure 3:
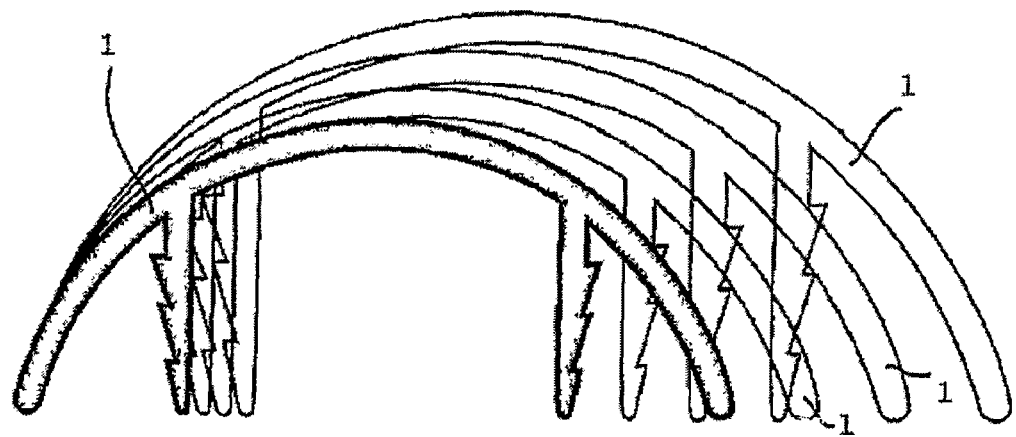
FIG. 3 is a view of a set of prostheses.

As mentioned above, the diameter of the crown may be a percentage of the diameter of the circular cylinder section. In this case a value of greater than 50%, particularly 55% to 65% and particularly 60%, is preferred. With a set of invention-specific prostheses of various, increasing size, the diameter of the crown thus increases, since in terms of size is coupled to the diameter of the spherical shell section. This is schematically depicted in FIG. 3, wherein a set of four prostheses 1 of varying sizes is depicted in a type of section depiction and with all four prostheses in the same figure, in which the crown diameter in each case is about 60% of the diameter (measured outside on the free edge) of the ball section.

While using the figures in essence only a preferred embodiment of the invention-specific prosthesis was described, to the specialist it is clear that most of the features presented vary in regard to their function, can be otherwise combined or deleted.

The invention claimed is:

1. A prosthesis for replacing a surface of a ball of a ball-and-socket joint comprising:
a spherical shell section having an outer surface that is configured to lie in an articular fossa and for attachment to a surface, the shell section having a cavity for receiving a bone end; and
a crown that partitions the cavity of the shell section into first and second cavities adapted to receive the bone end;
wherein the shell section comprises less than a hemisphere and a free edge of the crown lies in the same plane as a free edge of the shell section.

2. The prosthesis of claim 1, wherein the spherical shell section has a height (h) that is about 65% to 90% of a radius of the ball.

3. The prosthesis of claim 2, wherein the spherical shell section has a height (h) that is about 70% to 85% of the radius of the ball.

4. The prosthesis of claim 2, wherein the spherical shell section has a height (h) that is about 80% of the radius of the ball.

5. The prosthesis of claim 1, wherein the first cavity has a circular shape and the second cavity has an annular shape.

6. The prosthesis of claim 1, wherein an innermost end of the crown is integrally connected to an inner surface of the shell section so as to form a single integral structure.

7. The prosthesis of claim 1, wherein at least one of an inner surface of the shell section and a surface of the crown is configured for contact with the bone end and is therefore a roughened surface.

8. The prosthesis of claim 1, wherein the crown has at least one opening formed therein to provide communication between the first and second cavities.

9. The prosthesis of claim 8, wherein the at least one opening comprises at least five openings.

10. The prosthesis of claim 1, wherein at least one of an inner surface and an outer surface of the crown has a relief structure formed as a part thereof.

11. The prosthesis of claim 10, wherein the relief structure comprises a fluting that is formed by ring beads that extend circumferentially around the crown.

12. The prosthesis of claim 1, wherein the inner surface of the shell section includes a relief structure that extends along an edge of the shell section.

13. The prosthesis of claim 12, wherein the relief structure comprises fluting formed circumferentially around the inner surface of the shell section.

14. The prosthesis of claim 1, wherein the crown and shell section are separate parts and are constructed to be securely coupled to one another.

15. The prosthesis of claim 14, wherein the crown and shell section are constructed to be threadingly coupled to one another by means of threads formed on at least one of an outer surface of the crown and an inner surface of the shell section.

16. The prosthesis of claim 1, wherein the crown has a shape selected from the group consisting of a circle and a polygon.

17. The prosthesis of claim 1, wherein the crown is arrayed in a coaxial manner.

18. The prosthesis of claim 1, wherein the crown and shell section are individual parts and are connected to one another by a mechanical fit selected from the group consisting of screw threading, a bayonet joint and a clamping device.

19. A procedure for implantation of a prosthesis in a bone comprising the steps of:
   preparing the bone and forming a groove in the bone;
   providing a prosthesis for replacing a surface in an area of a ball of a ball-and-socket joint, the prosthesis including a spherical shell section and a crown, the shell section having an outer surface configured to lie in an articular fossa and for attachment to a surface, the shell section having a cavity for receiving a bone end, the crown partitioning the cavity of the shell section into a first cavity and a second cavity, wherein the shell section comprises less than a hemisphere and a free edge of the crown lies in the same plane as a free edge of the shell section; and
   inserting the prosthesis onto the bone such that the crown is received in the groove formed in the bone.

20. A set of prostheses comprising:
   a plurality of prostheses according to claim 1, wherein the shell sections are formed having diameters that differ from one another and wherein a ratio of a height (h) of the shell section to a respective ball diameter is equal for each prosthesis and wherein a diameter of each crown amounts to the same percentage of a diameter of the spherical shell section for each prosthesis.

* * * * *